United States Patent [19]

Brushwyler et al.

[11] 3,986,932

[45] Oct. 19, 1976

[54] CONTROL OF AEROBIC FERMENTATION PROCESSES

[75] Inventors: Gordon R. Brushwyler, Anaheim; Timothy F. Scott, Fullerton, both of Calif.

[73] Assignee: Robertshaw Controls Company, Richmond, Va.

[22] Filed: Mar. 21, 1975

[21] Appl. No.: 560,630

[52] U.S. Cl. .......................... 195/117; 195/103.5 R; 195/113; 195/139; 210/3; 210/15; 426/56
[51] Int. Cl.² ...................... C12B 1/00; C12K 1/04
[58] Field of Search ............. 195/103.5 R, 113, 127, 195/139, 117; 204/195 P; 318/591; 210/3, 5; 426/56

[56] References Cited
UNITED STATES PATENTS

| | | | |
|---|---|---|---|
| 3,684,702 | 8/1972 | Hartmann | 195/103.5 R |
| 3,813,325 | 5/1974 | Merrell et al. | 204/195 P |
| 3,845,376 | 10/1974 | Brushwyler et al. | 318/591 |

Primary Examiner—David M. Naff
Assistant Examiner—C. A. Fan
Attorney, Agent, or Firm—Fulwider, Patton, Rieber, Lee & Utecht

[57] ABSTRACT

Aerobic fermentation processes which involve mixing an aqueous microbial food medium with a microbial culture are controlled by continuously withdrawing a sample of the microorganism culture and a sample of a mixture of the aqueous food medium and the microorganism culture, directly and continuously measuring a respiration rate of both samples and proportionating the amount of the microorganism culture admixed with the food medium in response to the respiration rate measured to maintain a ratio of the biochemical oxygen demand of the food medium to that of the microorganism culture at a preselected constant value. This control process is preferably used when decomposing wastes such as sewage by aerobic microbial fermentation.

10 Claims, 2 Drawing Figures

CONTROL OF AEROBIC FERMENTATION PROCESSES

BACKGROUND OF THE INVENTION

1. Field of the Invention

This invention relates to a biochemical process and, in particular, relates to a method and enabling apparatus for control of an aerobic biochemical process.

2. Brief Statement of the Prior Art

There are a substantial number of biochemical processes which utilize bacteria, fungi, molds or actinomycetes for the industrial fermentation of wastes to innocuous or desired end products. Some of these processes include the bacterial production of proteins from hydrocarbons, vinegar from alcohol, citric acid from sucrose, and the disposal of industrial and municipal wastes by aerobic decomposition, typically with the activated sludge process. Representative of industrial wastes which are treated in this fashion are wastes of textile plants, rubber plants, canneries, dairies, meat packing plants, pulp and paper plants, etc.

All of the aforementioned biochemical processes, whether conducted batch-wise or continuously, require the admixing of a microbial food with a microbial culture which is in a food limited growth phase and contacting the mixture in a holding tank or vessel with a supply of oxygen to insure the rapid growth of the microorganism.

Commonly, the microbial culture utilized in the process is substantially depleted of a supply of microbial food and often is a recycle stream such as recycled sludge in an activated sludge process. This recycle of the aqueous microbial culture is usually performed at a constant weight or volume proportion to the incoming raw microbial food medium. A difficulty which is frequently encountered is that the recycled microbial culture is not of uniform and consistent activity. Thus, if the aqueous material being processed contains any inhibitors of microbial action, e.g., dissolved heavy metals or toxins, the microbial culture can have substantially lesser activity than expected and, accordingly, when recycled at a constant volume or weight mass, there results an inadequate innoculation of the incoming stream to insure its rapid and complete aerobic decomposition. A similar result occurs if the composition or concentration of microbial food in the aqueous microbial food medium changes materially.

Because biochemical processes are conducted in relatively dilute aqueous media and require substantial reaction times, there is a substantial time lag in the detection of any inhibition of activity of the recycle microbial culture or in the composition of the incoming microbial food medium. As a result, upsets in the process, particularly when conducted in a continuous fashion, have substantial and detrimental consequences in the operation.

BRIEF STATEMENT OF THE INVENTION

The invention provides a method for the control of a biochemical process utilizing aerobic microorganisms. This invention comprises the measurement of the respiration rate of the microorganism culture which is added to the aqueous medium containing the microbial food and proportionating the amount of the microorganism culture so added to maintain a constant ratio in the biochemical oxygen demand of the aqueous food media to the measured biochemical oxygen demand of the microorganism culture. When the invention is applied to a source of microbial food which is of uniform and consistent composition, the control can be affected simply by measurement of the respiration rate of the microorganism culture and measurement of the rate of supply of the raw microbial food. A continuous process can be monitored and controlled simply by measuring the incoming or exiting flow rate of the aqueous medium transporting the microbial food, the respiration rate of the microorganism culture and controlling the rate of its addition, typically, by flow control of the aqueous medium containing the microorganism culture.

The control of the invention can also be applied to biochemical processes that are supplied with a source of microbial food of varying or nonuniform composition or concentration. Typical of this would be the application of the process to secondary sewage treatment of municipal wastes. In this process, the respiration rate of the combined microorganism culture and aqueous medium containing the microbial food is determined to obtain a precise indication of the biochemical oxygen demand of the combined culture and food inputs. The biochemical oxygen requirement of the microorganism culture is then subtracted from the total biochemical oxygen demand so determined to obtain a precise indication of the biochemical oxygen demand of the incoming microbial food. The measured respiration rate of the microorganism culture is used to proportion the amount of the microorganism culture to the incoming microbial food and maintain the ratio of the biochemical oxygen demand of the microbial food medium to that of the microorganism culture at a preselected constant value.

BRIEF DESCRIPTION OF THE DRAWINGS

The invention will be described by references to the drawings of which.

DESCRIPTION OF PREFERRED EMBODIMENTS

Figure 1:
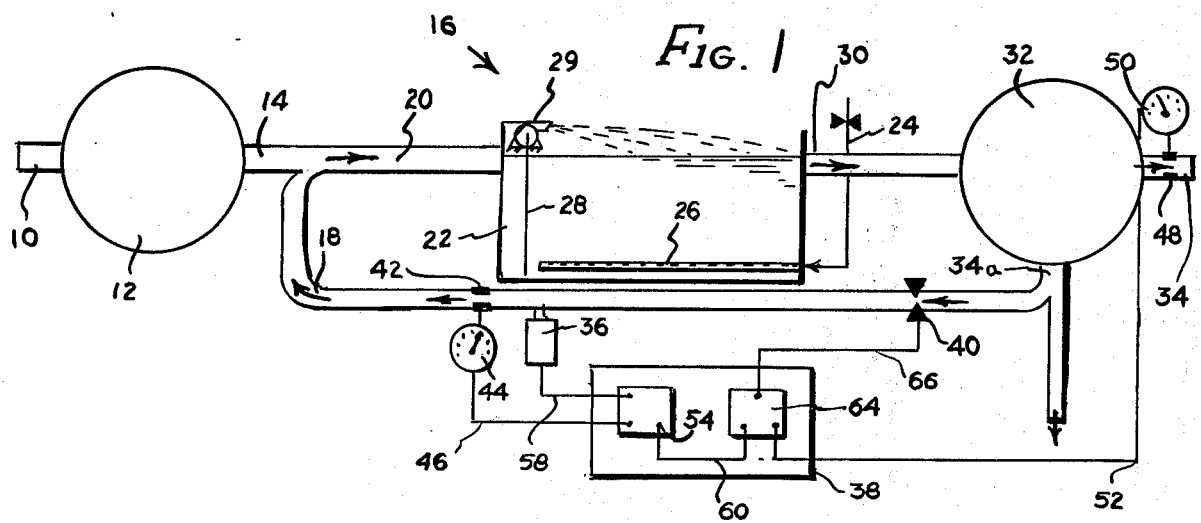
FIG. 1 illustrates the simplest embodiment of the invention as applied to an inlet stream of uniform and consistent composition and concentration of microbial food.

The invention is illustrated and described herein with regard to its application to the activated sludge process which is commonly used for the treatment of industrial and municipal waste waters to obtain a treated aqueous effluent that is suitable for return to the environment or that can be further purified by suitable tertiary treatment. Typically, the process comprises the treatment of the incoming raw sewage containing decomposible organic material through line 10 in a primary clarifier 12. Prior to the primary clarifiers, screens aree placed in a chamber or channel in the flow path of the incoming raw sewage in a manner permitting mechanical rakes and the like to remove the separated debris from the surface of the screens. The incoming sewage is then passed into a settling tank where grit such as sand, stones, cinders and the like settle. The resultant screened and settled effluent is passed through line 10 to continue primary treatment. The primary treatment in clarifier 12 comprises, chiefly, the removal of sediment and floatable material such as grease, that may cause obstruction of flow during subsequent treatment.

The resultant screened and clarified effluent is passed through line 14 to the secondary treatment.

The primary effluent is blended with recycled activated sludge from line 18 to obtain a blended stream 20 that flows into the aeration tanks or vessels 22 where the sewage and recycled activated sludge are contacted with oxygen, typically, air. Various techniques are employed for insuring adequate aeration of the sewage in the aeration vessels 22. In one method, air can be introduced under pressure through line 24 to the bottom of tank 22 and discharged therein through a sparger 26 to insure intimate contact with the liquid. Another technique of aeration which can be used is mechanical stirring, wherein the settled sewage from the bottom of vessel 22 is pumped through line 28 by pump 29 and sprayed across the surface of the liquid in the vessel 22, thereby contacting and saturating the sewage with air. Some treatment plants use the combination of these two techniques of aeration.

The treated sewage is withdrawn from the aeration tanks through line 30 and is clarified in clarifier 32 to separate a relatively clear, aqueous effluent through line 34 from the settled, activated sludge that comprises chiefly the population of microorganisms grown in the aeration vessel 22. The activated sludge so removed through line 34a is substantially depleted of microbial food that was consumed in the growth of the microorganism culture during its residence in vessel 22 and the activated sludge is in a declining growth phase of its life cycle, limited by food supply. In instances where the exogenous food supply is entirely depleted in the activated sludge, the microorganism culture undergoes endogenous metabolism.

The clarified aqueous effluent is removed from secondary clarifier 32 through line 34 and can be discharged as such or can be subjected to various treatments such as filtration, ozonation, chlorination or other treatment to obtain a sterile water that is acceptable for discharge to the surrounding watershed.

The invention as applied to the process thus described includes the determination of the respiration rate of the recycled microorganism culture, i.e., activated sludge in line 18. The respriation rate of the microorganism culture in the activated sludge recycled through line 18 is determined utilizing a continuous respirometer such as Robertshaw Model 970 available from Robertshaw Controls, Aeronautical and Instrument Division, 333 N. Euclid Way, Anaheim, California. This continuous respirometer is described in issued U.S. Pat. No. 3,813,325, which is incorporated herein by reference. Briefly, the continuous respirometer comprises an elongated residence tube with a small cross section and suitable flow control means for controlling the flow rate of a sample of the liquid under investigation through the tube. The device includes an aeration vessel where the incoming sample is substantially saturated with air before it is passed through the residence tube. Dissolved oxygen sensing means, in the form of electrolytic sensing probes, are positioned at the inlet and outlet of the residence tube to produce DC analog voltage signals in response to the dissolved oxygen content of the sample at the positions of the sensing probes. The resultant voltages are subtracted and amplified to provide a DC current analog signal that is directly responsive to the oxygen depletion of the sample between the inlet and outlet of the residence tube, thereby providing a direct indication of the respiration rate of the microorganism culture in the sample.

The analog DC current signal can be directly observed in a suitable read-out display on instrument 36 and can also be applied as a control signal through a control circuit, generally indicated at 38, to control the setting of flow control valve 40.

The flow rate of recycle sludge through line 18 is measured by a flow meter 42 which can be of any suitable construction such as a magnetic flow meter which can have a suitable display unit such as 44. The meter includes an induction coil which detects changes in flux of a magnetic field which is imposed about a section of line 18 such that changes in flow through line 18 disrupt the flux of the imposed magnetic field. The meter, preferably, develops a signal such as a DC analog current signal that is directed through line 46 to the control circuit 38. The net flow of liquid through the sewage treatment plant is also determined, preferably by a similar flow meter 48 that is positioned in the effluent stream in line 34. The meter 48 could be placed in other locations such as in the incoming raw sewage line 14, but is preferably located in the effluent line to avoid any erroneous readings or upsets that could be caused by suspended solids and debris in the incoming raw sewage. Flow meter 48 is preferably a meter that can accurately measure flow rates of solid suspensions such as a Robertshaw Series F flow measuring system consisting of a Parshall flume, flow transmitter and remote display unit 50. The Parshall flume is a free flow tubular box member described in U.S. Pat. No. 3,729,994 having a center section of reduced cross sectional area in which is mounted a capacitance level probe such as Robertshaw Probe Model 725, capable of generating a DC milliamp output signal in response to its depth of immersion which signal is proportional to the flow through the flume. The output signal is supplied through line 52 to control circuit 38.

Since the control system of FIG. 1 is applied to a sewage treatment process having an incoming sewage stream of substantially constant composition and concentration of raw microbial food, the signal developed by meter 48 is, therefore, directly proportional to the biochemical oxygen demand of the incoming stream.

The control circuit 38 comprises two basic modules 54 and 64. Module 54 comprises a solid state multiplier/divider such as Robertshaw Part 900-800-160. Briefly, this multiplier includes a fixed slope ramp pulse signal generator having a one shot pulse shaper timed by a fixed frequency multivibrator triggering a shunt switch in circuit to a charging capacitor. The capacitor is in circuit to the input of a pulse width convertor. One of the input signals, e.g., the analog current signal from meter 42 is connected to a multiplier input terminal of module 54. The signal goes through a voltage amplifier and then to a pulse width convertor to provide a pulse width signal proportional to the value of the input signal. The other input signal, from respirometer 36, is connected to the other multiplier input terminal of module 54 and supplied directly to a pulse height convertor that also receives the pulse signal from the pulse width convertor. The resultant pulse from the height convertor is fed into an integrator and converted to a DC analog voltage which controls an output DC current generator. The output of multiplier module 54 is a DC analog current signal that is proportional to the biochemical oxygen demand (multiple of flow rate times respiration rate) of the microorganism culture being recycled through line 18.

As previously mentioned, the microorganism culture in line 18 is in declining growth phase as limited by the depleted food supply in the treated sewage and, accordingly, this biochemical oxygen demand approaches that of the endogenous respiration of the microorganism culture.

The signal developed by amplifier 54 is passed through line 60 to the process variable input terminal of deviation control amplifier 64. The operation of the deviation control amplifier 64 is described in U.S. Pat. No. 3,845,376 which is incorporated herein by reference. The DC analog current signal from meter 48 is passed through line 52 to the setpoint input terminal of deviation control amplifier 64. The action of deviation control amplifier 64 is to maintain the process variable input signal obtained from lead 60 equal to the setpoint signal obtained from lead 52. This is accomplished by a DC analog current output signal being developed in deviation control amplifier of module 64 that is proportional to the deviation or difference between the signals supplied by leads 60 and 52. This output signal is fed through line 66 to flow control valve 40.

Control module 64 is set to develop a control signal transmitted through line 66 to cause flow control valve 40 to open and recycle greater quantities of activated sludge when the flow rate to the treatment plant increases or when the respiration rate of the recycled activated sludge decreases, or close the valve 40 and decrease the amount of recycled sludge when the corresponding opposite conditions occur. In this manner, a constant and preselected ratio between the biochemical oxygen demand of the microbial food medium to the biochemical oxygen demand of the microorganism culture can be maintained, independently of changes in activity or concentration of the microbial culture.

Figure 2:
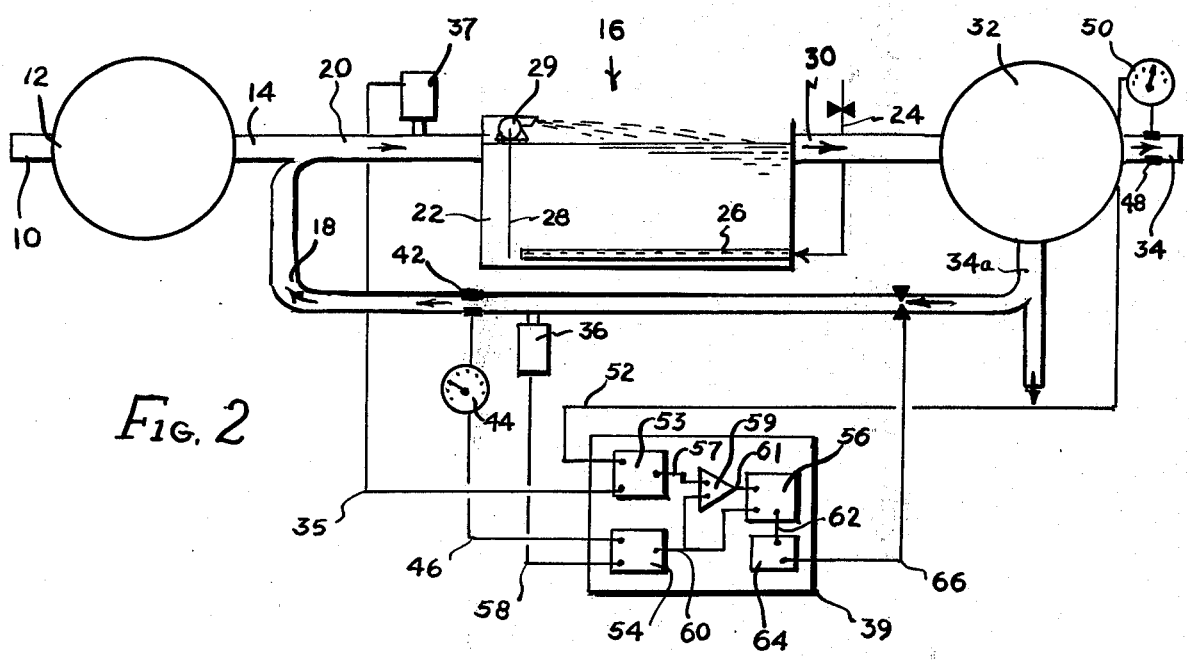
FIG. 2 illustrates the invention as applied to treatment of an incoming stream of varied composition and/or concentration of raw microbial food.

Referring now to FIG. 2, there is disclosed the application of the invention to treatment of sewage of variable composition or concentration. This treatment would be typical of the application of the invention for treatment of municipal sewage. As there illustrated, elements which are unchanged from those with regard to FIG. 1 bear identical numbers. The raw sewage is screened and settled and is introduced through line 10 tonprimary clarifier 12 to remove sediment and floating material such as grease.

The screened and clarified sewage after primary clarification is then passed through line 14 into admixture with the recycled, activated sludge received through line 18. The combined streams are passed through line 20 to the aeration vessel 22 which comprises a portion of the activated sludge process that is generally indicated at 16. The aeration is conducted by sparging of air introduced in line 24 and sparger 26 and/or by mechanical stirring of settled sewage through line 28 and pump 29 as previously described. After treatment in aeration vessel the sewage containing the increased microorganism population and depleted microbial food is removed through line 30 and passed to the secondary clarifier 32 where the microorganism culturre is separated as activated sludge that is removed through line 34a and a treated and clarified aqueous effluent removed through line 34.

The flow rate of sewage through the treatment plant 16 is measured by flow meter 48 and can be observed on visual indicator 50. The flow rate of the recycled activated sludge is measured by flow meter 42 and can be observed on indicator 44. A control valve 40 is placed in the activated sludge recycle line 18 for controlling the recycling of this sludge.

The continuous bacterial respirometer, such as the aforementioned Robertshaw Model 970, is provided to monitor the respiration rate of the recycled microorganism culture through line 18 by continuously withdrawing a sample of this recycle stream and processing it in the manner previously described. As thus described, the process of FIG. 2 is similar in its operation to that described with regard to FIG. 1.

The embodiment of FIG. 2 differs from that of FIG. 1, however, in the addition of a second bacterial respirometer 37 which is positioned in line 20 to monitor the respiration rate of samples withdrawn from the admixture of the recycled activated sludge from line 18 and the incoming raw sewage from line 14. This instrument 37 thereby produces a DC analog current signal which is proportional to the respiration rate of the combined streams. The signal developed by respirometer 37 is applied through line 35 to multiplier module 53 of the control system which is generally indicated at 39. Multiplying module 53 can be similar to that previously described with regard to element 54 of FIG. 1 and is operative to multiply the respiration rate signal received through line 35 by a DC analog current signal proportional to the net flow through the process which is generated by meter 48 and transmitted by line 52 to its other input terminal. This output signal is proportional to the biochemical oxygen demand of the combined recycle and primary effluent sewage streams in line 20, i.e., the multiple of flow rate and respiration rate. This signal is applied through line 57 to conventional differential amplifier 59.

Continuous respirometer 36 monitors a sample of the recycle sludge in line 18 and produces a DC analog current signal representative of the respiration rate of the microorganism culture in this sludge stream. Flow meter 42 senses the rate of flow of the recycle activated sludge and produces a DC analog current signal representative of that flow. These signals are applied through lines 58 and 46 to the input terminals of a multiplier module 54 such as previously described to obtain an output DC analog current signal that is representative of the biochemical oxygen demand of the recycled microorganism culture in line 18. This output signal is applied through line 60 to an input terminal of differential amplifier 59.

The differential amplifier 59 functions to subtract the two input signals supplied to its terminals and develop an output signal which is an analog of the biochemical oxygen demand of the incoming primary effluent sewage in line 14. This signal is applied through line 61 to an input of divisional module 56 which can be another multiplier/divider unit such as that described with regard to unit 54. The signal of line 61 is supplied to the first multiplier input terminal of multiplier/divider module 56.

The output of multiplying module 54 is applied to the divisional input terminal of the multiplier/divider module 56. This signal is amplified and supplied to the charging capacitor to change the capacitor charging rate, and hence ramp slope, in proportion to the value of the input divisional signal from line 60. This results in generation of a pulse width signal having a width proportional to the value of the signal from line 57 divided by the value of the signal from line 60. The pulse signal is processed through the integrator and DC current generator to provide an output signal at lead 62 which is analog of the ratio of: the biochemical oxygen demand of the decomposable organic material in the incoming primary effluent sewage stream supplied through line 14 to the biochemical oxygen demand of the food-limited microorganism culture recycled in the activated sludge recycle line 18. This signal is applied through line 62 to a comparator module 64 which is similar to that previously described with regard to FIG. 1 and which has set point at a preselected value of the aforesaid ratio. The comparator unit 64 is operative to generate a control signal that is applied through line 66 to control valve 40, opening and closing this control valve in response to decreases or increases, respectively in the activity of the recycle culture or opening or closing this control valve in response to the increases or decreases, respectively, of decomposable organic material in the incoming primary effluent sewage stream entering the process through line 14.

When meter 48 is located on the outlet effluent stream, as shown, a slight discrepancy can occur in that the signal generated is proportional to net, rather than total flow through the secondary process. Since the volume of the recycle sludge stream is only a minor amount of the net flow, e.g., from 5 to about 20 percent, this is not significant. If desired, a more precise control could be obtained by electronically summing the rate signals of meters 48 and 42 and using the summed signal as the input signal transmitted by line 52 to multiplier module 53. Alternatively, meter 48 could be relocated to line 20, however, this would require use of a flow meter such as meter 42 that can accurately measure flow rates of fluid suspensions.

The aforedescribed control process has the advantage of providing a precise and reliable control of a biochemical process. The control is particularly advantageous in such a process since the relatively slow reaction rates and large residence volumes encountered in such processes prevent rapid detection of upset conditions such as changes in the composition or concentration of the decomposable organic material in the incoming sewage for treatment or unanticipated inhibitions of microbial activity caused by the presence of inhibitors or toxins to the microorganisms.

Because the process provides a continuous monitoring of the respiration rate of the food-limited microorganism cultrue, a continuous, reliable indication of the microbial activity of this culture is provided to permit a facile and precise control of the activated sludge process. In the application where substantial variations in composition and/or concentration of the decomposable organic matter of the incoming stream are encountered, the control system also provides the capability for monitoring the parameter of critical importance to operation of the process, i.e., the actual biochemical oxygen demand that will be encountered when the stream is treated in the process. The value of the preselected ratio of biochemical oxygen demand of microbial food medium to that of the microorganism culture for most biochemical processes will generally be from about 0.1 to 1.0, and preferably will be from 0.2 to 0.5. The actual value can be determined emperically by optimizing the process. An activated sludge process can be optimized to produce an effluent having a minimal biochemical oxygen demand.

The invention has been described with reference to the presently preferred and illustrated embodiments thereof. It is not intended that the invention be unduly limited by this disclosure of presently preferred embodiments. Instead, it is intended that the invention be defined by the means steps and their obvious equivalents set forth in the following claims.

What is claimed is:
1. The method for controlling a continuous biochemical process utilizing aerobic microorganisms which comprises the continuous process steps of:
   a. introducing into the process an aqueous food medium therefore containing decomposable organic material including suspended solids and debris as the source of microbial food; and
   b. admixing therewith a microorganism culture to obtain a combined aqueous food medium and microorganism culture;
   c. contacting the combined medium and culture with oxygen to perform the biochemical process; said method also including the process control steps of:
   d. continuously withdrawing a sample of microorganism culture;
   e. continuously withdrawing sample of the combined aqueous food medium and microorganism culture;
   f. directly and continuously measuring the respiration rate of the sample of microorganism culture;
   g. directly and continuously measuring the respiration rate of the sample of combined aqueous food medium and microorganism culture; and
   h. proportionating the amount of the microorganism culture added in process step (b) to the amount of food medium added in process step (a) in response to the respiration rate measured in process control steps (f) and (g) to maintain the ratio of the biochemical oxygen demand of said decomposable organic material to that of said microorganism culture at a preselected constant value.

2. The method of claim 1 applied to a continuous flow biochemical process wherein said step of proportionating in process control step (h) is performed by measuring the process flow rates of said aqueous food medium and said microorganism culture and including the step of controlling the process flow rate of at least one of said medium and culture in response to the measure flow rate and respiration rates.

3. The method of claim 1 wherein said biochemical process is an activated sludge process for the treatment of sewage and said microorganism culture comprises activated sludge separated from the treated effluent of said process and recycled into admixture with the incoming sewage.

4. The method of claim 2 wherein said microorganism culture is substantially depleted of decomposable organic food and said observed respiration rate is the endogenous respiration rate of said microorganism culture.

5. The method of claim 3 applied to a continuous flow biochemical process wherein said step of proportionating in process control step (h) is performed by measuring the flow rates of said aqueous food medium and said microorganism culture and including process control step of controlling the flow rate of at least one of said medium and culture in response to the measured flow and respiration rates.

6. The method of claim 3 wherein said microorganism culture is substantially depleted of decomposable organic food and said observed respiration rate is the endogenous respiration rate of said microorganism culture.

7. The method of claim 2 which comprises generating first and second signals representative of the biochemical oxygen demands of the sample of microorganism culture and the combined aqueous food medium and sample of microorganism culture streams by multiplying the flow rates times the respiration rates for each of the aforesaid respective streams, generating a difference signal by subtracting the first from the second of the aforesaid signals and dividing the difference signal by the first signal to obtain a process control signal and controlling the flow rate of at least one of said medium and culture in response to said control signal.

8. The method of claim 3 which comprises generating first and second signals representative of the biochemical oxygen demands of the sample of microorganism culture and the combined aqueous food medium and sample of microorganism culture streams by multiplying the flow rates times the respiration rates for each of the aforesaid respective streams, generating a difference signal by subtracting the first from the second of the aforesaid signals and dividing the difference signal by the first signal to obtain a process control signal and controlling the flow rate of at least one of said medium and culture in response to said control signal.

9. The method of claim 1 wherein the flow rate of the aqueous food medium is indirectly determined by displacing from the process a treated effluent stream at an equal volumetric flow to the flow of said aqueous food medium and measuring the flow of said treated effluent.

10. The method of claim 3 wherein the flow rate of the aqueous food medium is indirectly determined by displacing from the process a treated effluent stream at an equal volumetric flow to the flow of said aqueous food medium and measuring the flow of said treated effluent.

* * * * *